(12) United States Patent
Kurosaki et al.

(10) Patent No.: US 8,269,035 B2
(45) Date of Patent: Sep. 18, 2012

(54) PROCESS FOR PRODUCTION OF RADIOACTIVE-FLUORINE-LABELED ORGANIC COMPOUND

(75) Inventors: Fumie Kurosaki, Sodegaura (JP); Masahito Toyama, Sodegaura (JP); Akio Hayashi, Sodegaura (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 0 days.

(21) Appl. No.: 12/747,726

(22) PCT Filed: Dec. 16, 2008

(86) PCT No.: PCT/JP2008/072827
§ 371 (c)(1),
(2), (4) Date: Jun. 11, 2010

(87) PCT Pub. No.: WO2009/078396
PCT Pub. Date: Jun. 25, 2009

(65) Prior Publication Data
US 2010/0261931 A1    Oct. 14, 2010

(30) Foreign Application Priority Data
Dec. 19, 2007  (JP) ................................. 2007-327444

(51) Int. Cl.
    C07C 69/74    (2006.01)
(52) U.S. Cl. ..................................................... 560/123
(58) Field of Classification Search ........................ None
See application file for complete search history.

(56) References Cited

U.S. PATENT DOCUMENTS

| | | | |
|---|---|---|---|
| 5,808,146 | A | 9/1998 | Goodman et al. |
| 5,817,776 | A | 10/1998 | Goodman et al. |
| 6,190,637 | B1 | 2/2001 | Ino et al. |
| 6,919,475 | B2 | 7/2005 | Hamacher |
| 2004/0192954 | A1 | 9/2004 | Hamacher |
| 2006/0292073 | A1 | 12/2006 | Goodman et al. |
| 2009/0030192 | A1 | 1/2009 | Hirano et al. |
| 2009/0198085 | A1* | 8/2009 | Hayashi et al. ............... 562/505 |

FOREIGN PATENT DOCUMENTS

| | | |
|---|---|---|
| JP | 11-295494 A | 10/1999 |
| JP | 2000-500442 T | 1/2000 |
| JP | 2004-529989 T | 9/2004 |
| WO | WO 2004/056725 A1 | 7/2004 |
| WO | 2007/063940 A1 | 6/2007 |
| WO | 2007/132689 A1 | 11/2007 |

OTHER PUBLICATIONS

PCT International Preliminary Report on Patentability dated Jul. 20, 2010.
Supplementary European Search Report, dated Oct. 26, 2010 in EPO Application 08863261.7.
Office Action dated Oct. 1, 2010, in Russian Application 2008126277/04(032044) (Russian translation).
Communication from European Patent Office in EP Application 06833463.0, dated Jul. 14, 2010.
Examination Report issued Feb. 17, 2010 in New Zealand Application No. 568179.
Lijuan J. Wang et al., "Syntheses of New Conformationally Constrained S-[2-[(1-Iminoethyl)amino]ethyl]homocysteine Derivatives as Potential Nitric Oxide Synthase Inhibitors", Heteroatom Chemistry, vol. 13, No. 1, pp. 77-83 (2002).
Laurent Martarello et al., "Synthesis of syn* and anti-1-Amino-3-[18F]fluoromethyl-cyclobutane-1-carboxylic Acid (FMACBC), Potential PET Ligands for Tumor Detection", Journal of Medicinal Chemistry, vol. 45, No. 11, pp. 2250-2259 (2002).
Timothy M. Shoup et al., "Synthesis of [$^{18}$F]1-Amino-3-fluorocyclobutane-1-carboxylic Acid (FACBC): A Pet Tracer for Tumor Delineation", The Journal of Labelled Compounds and Radiopharmaceuticals, 42(3):215-225 (1999).
Timothy M. Shoup et al., "Synthesis and Evaluation of [$^{18}$F]1-Amino-3-fluorocyclobutane-1-carboxylic Acid to Image Brain Tumors", The Journal of Nuclear Medicine, vol. 40, No. 2, 331-338 (1999).
Examination Report issued Feb. 11, 2011, in corresponding New Zealand application 586636.
International Search Report issued on Feb. 10, 2009 in International Application No. PCT/JP2008/072827.
Shoup, T.M., et al. "Synthesis and Evaluation of [18F]1-Amino-3-fluorocyclobutane-1-carboxylic Acid to Image Brain Tumors." The Journal of Nuclear Medicine, 1999, vol. 40, No. 2, pp. 331-338.
McConathy, J., et al. "Improved synthesis of anti-[18F]FACBC: improved preparation of labeling precursor and automated radiosynthesis." Applied Radiation and Isotopes, 2003, vol. 58, No. 6, pp. 657-666.
Office Action dated Apr. 5, 2012 issued against AU Patent Application 2008339435.

* cited by examiner

Primary Examiner — Sudhakar Katakam
(74) Attorney, Agent, or Firm — Fitch, Even, Tabin & Flannery, LLP

(57) ABSTRACT

A process for production of a radioactive fluorine-labeled organic compound is provided which can improve the yield of radioactive fluorination. Provided is a process in which a compound represented by the following formula (1):

(1)

$$R^2O-\underset{CO_2R^1}{\overset{NR^3}{\diamondsuit}}$$

(wherein $R^1$ is a straight or branched alkyl chain with 1-10 carbon atoms or an aromatic substituent, $R^2$ is a straight or branched haloalkylsulfonic acid substituent with 1-10 carbon atoms, a straight or branched alkylsulfonic acid substituent with 1-10 carbon atoms, a fluorosulfonic acid substituent or an aromatic sulfonic acid substituent, and $R^3$ is a protective group) is heated under stirring in an inert organic solvent in a presence of a phase transfer catalyst, $^{18}$F ions and potassium ions, so as to effect labeling with a radioactive fluorine, wherein the heating temperature is 40-90° C., and the concentration of the phase transfer catalyst in the inert organic solvent is 70 mmol/L or more. Preferably, the molar ratio of the phase transfer catalyst is 0.7 or more relative to the compound of the formula (1), and the concentration of the compound of the formula (1) in the inert organic solvent is 50 mmol/L or more.

13 Claims, 2 Drawing Sheets

PROCESS FOR PRODUCTION OF RADIOACTIVE-FLUORINE-LABELED ORGANIC COMPOUND

CROSS-REFERENCE TO RELATED APPLICATIONS

This application is a National Phase Entry of International Application No. PCT/JP2008/072827, filed Dec. 16, 2008, which claims foreign priority to Japanese Patent Application No. 2007-327444, filed Dec. 19, 2007. The complete disclosures of the referenced applications are incorporated herein by reference.

TECHNICAL FIELD

The present invention relates to a process for producing a radioactive fluorine-labeled compound which can be suitably used for positron emission tomography and single photon emission computed tomography.

BACKGROUND ART

Nuclear medicine examination represented by positron emission tomography (hereinafter referred to as PET) and single photon emission computed tomography (hereinafter referred to as SPECT), is effective in diagnosing a variety of diseases including heart disease and cancer. These techniques involve administering an agent labeled with a specific radioisotope (hereinafter referred to as radiopharmaceutical), followed by detecting γ-rays emitted directly or indirectly from the agent. Nuclear medicine examination is characteristic in that it has not only such superior performances as high specificity and sensitivity to diseases, but also an advantage of providing information on the functionality of lesions, compared to other examination techniques.

For example, [$^{18}$F]2-fluoro-2-deoxy-D-glucose (hereinafter referred to as "$^{18}$F-FDG"), one of radiopharmaceuticals used for PET examination, tends to be concentrated in area where glucose metabolism is enhanced, thereby making it possible to specifically detect tumors in which glucose metabolism is enhanced.

Nuclear medicine examination is performed by tracing a distribution of an administered radiopharmaceutical, and data obtained therefrom vary depending on nature of the radiopharmaceutical. Thus, different radiopharmaceuticals have been developed for different diseases, and some of them are put into clinical use. There have been developed, for example, various tumor diagnostic agents, bloodstream diagnostic agents and receptor mapping agents.

In recent years, a series of radioactive halogen-labeled amino acid compounds including [$^{18}$F]1-amino-3-fluorocyclobutanecarboxylic acid (hereinafter referred to as [$^{18}$F]FACBC) have been designed as novel radiopharmaceuticals, and their clinical application is under examination (Patent Document 1, and non-Patent Documents 1 and 2). [$^{18}$F]FACBC is considered to be effective as a diagnostic agent for highly proliferative tumors, because it has a property of being taken up specifically by amino acid transporter.

As processes for producing [$^{18}$F]FACBC, there are disclosed processes which include: providing 1-(N-(t-butoxycarbonyl)amino)-3-[((trifluoromethyl)-sulfonyl)oxy]-cyclobutane-1-carboxylic acid ester as a labeling precursor, substituting the triflate group at position 3 of the precursor with radioactive fluorine, and carrying out deprotection by subjecting the resulting compound to an acidic condition (Patent Document 1, and non-Patent Documents 1 and 2).

Patent Document 1: Japanese Patent Laid-open No. 2000-500442.
Non-Patent Document 1: Jonathan McConathy et al., "Improved synthesis of anti-[18F]FACBC: improved preparation of labeling precursor and automated radiosynthesis.", Applied Radiation and Isotopes, (Netherlands), 2003, 58, p. 657-666.
Non-Patent Document 2: Timothy M. Shoup et al., "Synthesis and Evaluation of [18F]1-Amino-3-fluorocyclobutane-1-carboxylic Acid to Image Brain Tumors.", The Journal of Nuclear Medicine, 1999, 40, p. 331-338.

DISCLOSURE OF THE INVENTION

Problems to be Solved by the Invention

However, production yield has been 12-24% in the process for producing [$^{18}$F]-FACBC disclosed until now (J. McConathy et al., Applied Radiation and Isotopes, 2003, 58, p. 657-666). It is desired that a condition that can stably provide a higher yield is used in order to produce [$^{18}$F]-FACBC industrially.

The production of [$^{18}$F]-FACBC comprises, as main steps, a radioactive fluorinating step of adding a radioactive fluorine to a labeling precursor and a deprotecting step of conducting deprotection of the intermediate compound produced by the radioactive fluorinating step. According to the conventional process, the radioactive fluorinating step shows a yield of 12-42% (Japanese Patent Laid-open No. 2000-500442, and Timothy M. Shoup et al., J. Nuc. Med., 1999, 40, p. 331-338), and the low yield in this step is one of the causes that lower the synthesis yield of [$^{18}$F]-FACBC. Therefore, in order to improve the synthesis yield of [$^{18}$F]-FACBC, the yield in the radioactive fluorinating step should be first improved.

The present invention has been made in view of the above described circumstances, and aimed at providing a production process which can stably provide a radioactive fluorine-labeled amino acid such as [$^{18}$F]1-(N-(t-butoxycarbonyl)amino)-3-fluorocyclobutane-1-carboxylic acid ester (hereinafter referred to as [$^{18}$F]-FACBC) as an intermediate of [$^{18}$F]FACBC.

Means for Solving the Problems

As a result of investigation, the present inventors have found that a radioactive fluorine-labeled amino acid such as [$^{18}$F]-FACBC can stably be obtained in high yield by setting a reaction temperature at 40-90° C. and a concentration of the phase transfer catalyst in the reaction solution at not less than a specific amount during the radioactive fluorinating reaction, and thus the present invention has been completed.

Therefore, according to the present invention, a process for producing a radioactive fluorine-labeled organic compound is provided, which comprises subjecting a compound represented by the following formula (1):

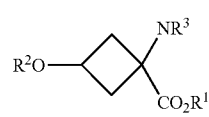

to a heating step in an inert organic solvent in a presence of a phase transfer catalyst, $^{18}$F ions and potassium ions, so as to obtain a compound represented by the following formula (2):

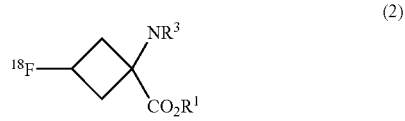

(2)

in which the heating step is conducted at a heating temperature of 40-90° C., and the phase transfer catalyst is contained in the inert organic solvent at a concentration of not less than 70 mmol/L.

In the producing process of the present invention, potassium ions subjected to the heating step are preferably contained in the inert organic solvent at a concentration of not less than 27 mmol/L.

Also, in the producing process of the present invention, the phase transfer catalyst is used in a molar ratio of not less than 0.7 relative to the compound represented by the formula (1).

Further, in the process for producing of the present invention, the compound represented by the formula (1) is contained in the inert organic solvent at a concentration of not less than 50 mmol/L.

According to a preferable embodiment of the present invention, the producing process of the radioactive fluorine-labeled organic compound according to the present invention comprises;

a step of obtaining a mixture of a phase transfer catalyst, $^{18}F$ ions and potassium ions; and a radioactive fluorinating step of adding a compound represented by the formula (1) and an inert organic solvent to the above mixture, and maintaining the resulting reaction solution at a temperature of 40-90° C. under stirring so as to obtain a compound represented by the formula (2).

In the above formulae (1) and (2), $R^1$ is a straight or branched alkyl chain with 1-10 carbon atoms or an aromatic substituent, and preferably can be a substituent selected from the group consisting of methyl group, ethyl group, t-butyl group and phenyl group.

$R^2$ is selected from the group consisting of a straight or branched haloalkylsulfonic acid substituent with 1-10 carbon atoms, a straight or branched alkylsulfonic acid substituent with 1-10 carbon atoms, a fluorosulfonic acid substituent and an aromatic sulfonic acid substituent, and preferably can be a substituent selected from the group consisting of methane sulfonic acid, toluene sulfonic acid, nitrobenzene sulfonic acid, benzene sulfonic acid, trifluoromethane sulfonic acid, fluoro sulfonic acid and perfluoroalkyl sulfonic acid.

$R^3$ is a protective group, and is not particularly limited as long as it can prevent the reaction between a radioactive fluorine and an amino group. Concretely, it is selected from the group consisting of various carbamate substituents, various amide substituents, various imide substituents and various amine substituents, and preferably a straight or branched alkyloxycarbonyl substituent with 2-7 carbon atoms, a straight or branched alkenyloxycarbonyl substituent with 3-7 carbon atoms, a benzyloxycarbonyl substituent with 7-12 carbon atoms which may have a substituent, an alkyldithiooxycarbonyl substituent with 2-7 carbon atoms, a straight or branched alkylamide substituent with 1-6 carbon atoms, a straight or branched alkenylamide substituent with 2-6 carbon atoms, a benzamide substituent with 6-11 carbon atoms which may have a substituent, a cyclic imide substituent with 4-10 carbon atoms, an aromatic imine substituent with 6-11 carbon atoms which may have a substituent, a straight or branched alkylamine substituent with 1-6 carbon atoms, a straight or branched alkenylamine substituent with 2-6 carbon atoms, and a benzylamine substituent with 6-11 carbon atoms which may have a substituent. More preferably, $R^3$ is one selected from the group consisting of t-butoxycarbonyl group, allyloxycarbonyl group, phthalimide group and N-benzylideneamine substituent, and most preferably, t-butoxycarbonyl group or phthalimide group.

In the producing process of a series of radioactive fluorine-labeled amino acids such as $[^{18}F]$-FACBC disclosed until now, the radioactive fluorine-labeling reaction was performed using a phase transfer catalyst at a low concentration, i.e., in a molar ratio of about 0.3 relative to a labeling precursor (Japanese Patent Laid-open No. 2000-500442, Timothy M. Shoup et al., J. Nuc. Med., 1999, 40, p. 331-338, and J. McConathy et al., Applied Radiation and Isotopes, 2003, 58, p. 657-666). Unlike such a conventionally disclosed process, the present inventors have found that the concentration of the phase transfer catalyst in the inert organic solvent is set at not less than 70 mmol/L, and preferably the phase transfer catalyst is used in a molar ratio of not less than 0.7 relative to the labeling precursor, whereby fluorination yield is remarkably improved, and a radioactive fluorine-labeled organic compound such as $[^{18}F]$-FACBC can be stably be produced in high yield. The amount of the phase transfer catalyst is preferably equimolar or more in terms of molar ratio relative to the labeling precursor.

In addition, the present inventors have found that radioactive fluorination yield in the radioactive fluorinating step can be improved by increasing a concentration of a labeling precursor in the reaction solution. Based on this finding, they have found that a radioactive fluorine-labeled amino acid such as $[^{18}F]$-FACBC can be produced in higher yield by setting a concentration of the labeling precursor in the inert organic solvent at not less than a certain concentration.

That is, a process according to another preferable embodiment of the present invention comprises maintaining the concentration of the labeling precursor in the inert organic solvent at not less than a certain concentration in the above described process for producing a radioactive fluorine-labeled organic compound. More concretely, the concentration of the precursor in the inert organic solvent is preferably not less than 50 mmol/L, more preferably not less than 60 mmol/L, and particularly preferably not less than 70 mmol/L.

Meanwhile, the higher the concentration of the labeling precursor in the inert organic solvent is, the higher the yield of the radioactive fluorinating step is; however, since an increase of the concentration of the precursor with the amount of the precursor being constant leads to decrease of the total volume of the solution, the concentration should be one that can ensure a sufficient amount of liquid to perform radioactive fluorinating reaction. The upper limit of such a concentration is determined by an amount of a labeling precursor to be used, a volume of the reaction vessel, and so on. For example, when production was conducted using an automatic synthesis device, the upper limit of the concentration of the reaction solution is 250 mmol/L if the lower limit of the liquid volume that can be treated in a reaction vessel is 0.4 mL and an amount of a labeling precursor to be used for the reaction is 0.1 mol. Similarly, the upper limit of the concentration of the reaction solution is 160 mmol/L if the lower limit of the liquid volume that can be treated in a reaction vessel is 0.5 mL and an amount of a labeling precursor to be used for the reaction is 0.08 mmol.

As mentioned above, the reaction temperature in the labeling reaction is 40-90° C. The reaction temperature lowers the reaction yield when it is too high or too low. A more preferable range of the reaction temperature is 50-80° C., and further preferably 60-70° C.

In the present invention, various solvents which do not have reactivity with the [$^{18}$F]fluoride ion, the phase transfer, the potassium ion, and the labeling precursor compound are usable as the inert organic solvent. Concrete examples of the inert organic solvent include organic solvents comprising at least one selected from the group consisting of tetrahydrofuran, 1,4-dioxane, acetone, 2-butanone, dimethylformamide, dimethylsulfoxide and acetonitrile, and preferably acetonitrile.

Effects of the Invention

According to the producing process of the present invention, the reaction temperature is set at 40-90° C. and a concentration of the phase transfer catalyst is maintained at not less than 70 mmol/L in the radioactive fluorination, preferably with the concentration of potassium ion and/or a labeling precursor in the inert organic solvent being maintained at a specific concentration or more and a molar ratio of the phase transfer catalyst relative to the labeling precursor being maintained at a specific amount or more, and thus the yield of production of the radioactive fluorine-labeled amino acid such as [$^{18}$F]Boc-FACBC can be improved.

BEST MODE FOR CARRYING OUT THE INVENTION

Hereinafter, a process for producing a radioactive fluorine-labeled organic compound according to the present invention will be described in detail taking, as an example, synthesis of [$^{18}$F]Boc-FACBC using 1-(N-(t-butoxycarbonyl)amino)-3-[((trifluoromethyl)-sulfonyl)oxy]-cyclobutane-1-carboxylic acid ethyl ester as a labeling precursor.

According to a preferable embodiment, the production process of the present invention comprises (1) a step of obtaining a mixture containing a phase transfer catalyst, $^{18}$F ions and potassium ions, and (2) a step of obtaining a radioactive fluorine-labeled organic compound by reacting a labeling precursor with the above mixture so as to effect a radioactive fluorine labeling (radioactive fluorinating step).

In the above step (1), radioactive fluorine can be obtained by a known method, for example, a method in which H$_2$$^{18}$O enriched water is used as a target and exposed to proton bombardment. In this instance, radioactive fluorine exists in the H$_2$$^{18}$O enriched water used as a target. The H$_2$$^{18}$O enriched water containing radioactive fluorine is allowed to pass through an anion-exchange column so that the radioactive fluorine is adsorbed and collected on the column, thereby being separated from the H$_2$$^{18}$O enriched water. Thereafter, a potassium carbonate solution is allowed to pass through the column to elute the radioactive fluorine, and the eluate is supplemented with a phase transfer catalyst and is evaporated to dryness, thereby obtaining a mixture containing a phase transfer catalyst, $^{18}$F ion and potassium ion.

The amount of potassium carbonate to be used here is preferably adjusted to 27 mmol/L or more in terms of concentration of potassium ions in the inert organic solvent used for the reaction solution. As it is clear from the Comparative Examples and Examples mentioned later, at a concentration of potassium ion in the inert organic solvent of less than 27 mol/L, the yield of [$^{18}$F] fluorination in the radioactive fluorinating step increases together with the concentration of the potassium ion, and at 27 mmol/L or more, it becomes almost constant. Therefore, the use of the condition under which the concentration of potassium ion in the inert organic compound is 27 mmol/L or more makes it possible to more stably perform the radioactive fluorinating step in high yield.

On the other hand, it should be noted that when the amount of potassium carbonate is excessive, a reaction product may decompose due to the influence of carbonate ions. In a preferable embodiment, an amount of potassium carbonate in terms of potassium ions may be about equivalent to that of a phase transfer catalyst, and it is most preferable that concentration and amount of the potassium carbonate solution are adjusted so that the amount of the phase transfer catalyst is about 1.3 in molar ratio relative to potassium ions.

Various compounds having a property to form a clathrate with $^{18}$F ion may be used as a phase transfer catalyst. Specifically, various compounds used for the production of organic compounds labeled with radioactive fluorine may be used; 18-crown-6 and other various aminopolyethers may be used. In the most preferable embodiment, KRYPTOFIX 222 (trade name, manufactured by Merck & Co., Inc.) may be used.

In the present invention, the amount of the phase transfer catalyst is adjusted so as to provide a concentration of not less than 70 mmol/L in the inert organic solvent which is added later. As it is clear from Comparative Examples and Examples which are described later, the radioactive fluorinating step can stably be performed in high yield by setting the amount of the phase transfer catalyst at not less than 70 mmol/L in the inert organic solvent. The amount of the phase transfer catalyst is preferably not less than 0.7 in terms of molar ratio relative to the labeling precursor which is used later in the radioactive fluorinating step. In a further preferable embodiment, the amount of the phase transfer catalyst is equimolar or more relative to the labeling precursor. In this instance, the larger the amount of the phase transfer catalyst is, the higher the yield becomes, but an excessive amount thereof is not preferable because it is often difficult to sufficiently remove the excessively-added phase transfer catalyst. In a preferable embodiment, the total amount of the phase transfer catalyst may be 0.2 mmol or less, for example, when the amount of the labeling precursor to be used is 80 μmol, the molar ratio of the phase transfer catalyst to the labeling precursor is 2.5 or less. This amount of the phase transfer catalyst can be easily removed by purification using a solid phase column or the like in a subsequent step.

After the mixture containing the phase transfer catalyst, [$^{18}$F] ions and potassium ions is obtained in the above way, the radioactive fluorine-labeled amino acid is synthesized by performing the above step (2). In this step, the labeling precursor 1-(N-(t-butoxycarbonyl)amino)-3-[((trifluoromethyl)sulfonyl)oxy]-cyclobutane-1-carboxylic acid ester is first added to the mixture containing the phase transfer catalyst, [$^{18}$F] ions and potassium ions. In the most preferable embodiment, the labeling precursor is previously dissolved in an inert organic solvent, and then added to the mixture. In this instance, it is preferred that the amount of the inert organic solvent to be used is adjusted so that the concentration of the labeling precursor in the reaction solution under the radioactive fluorination becomes not less than 50 mmol/L, because the yield in the radioactive fluorination is significantly improved.

After the addition of the labeling precursor and the inert organic solvent has been completed, the above reaction solution is subjected to radioactive fluorination by heating under stirring to obtain a radioactive fluorine-labeled organic compound as a target compound of the present invention. The reaction temperature is 40-90° C., preferably 50-80° C., and particularly preferably 60-70° C. The reaction time depends on the reaction temperature, and when the reaction temperature is 40-90° C., the reaction time is usually 3 minutes or longer, preferably 3-15 minutes, and more preferably 3-7 minutes. The longer the reaction time is, the further the labeling reaction with the radioactive fluorine is expected to proceed, but it should be noted that the decay of the radioactive fluorine proceeds simultaneously.

After the completion of reaction, purification is performed so as to remove unreacted raw materials and phase transfer catalysts. In the most preferable embodiment, purification is performed according to the following procedures. First, a solution is prepared by adding diethylether to the reaction solution that has completed the reaction. This solution is passed through the silica gel-based solid column (for example, Sep-Pak (registered trade mark) Silica (trade name, manufactured by Japan Waters) so as to obtain [$^{18}$F]Boc-FACBC in a form of a diethylether solution.

EXAMPLE

Hereinafter, the present invention is described in more detail by way of Examples and Comparative Examples which do not restrict the present invention.

Meanwhile, in Examples and Comparative Examples, radiochemical purity was determined by carrying out TLC analysis under the following conditions and using the following equation (1).

TLC analysis conditions:
Mobile phase: Diethylether/hexane=3/2
TLC plate: Silica Gel 60 $F_{254}$ (trade name, thickness of membrane: 0.25 mm, manufactured by Merck & Co., Inc.)
Mobile length: 10 cm
TLC scanner: Rita Star (manufactured by Raytest)

$$\text{Radiochamical purity (\%)} = \frac{\text{radioactivity of } [^{18}F] \text{ Boc-FACBC-OEt peak}}{\text{total radioactivity on TLC plate}} \times 100 \quad (1)$$

In addition, a yield of [$^{18}$F]fluorination was determined by the following equation (2).

$$\text{Yield of } [^{18}F] \text{ fluorination (\%)} = \frac{B}{A} \times \text{ radiochemical purity} \quad (2)$$

A: radioactivity of a mixture containing a phase transfer catalyst, [$^{18}$F], ions and potassium ions (MBq)
B: radioactivity of a synthesized [$^{18}$F]Boc-FACBC (MBq)

Reference Example 1

Synthesis of syn-1-(N-(t-butoxycarbonyl)amino)-3-[((trifluoromethyl)sulfonyl)oxy]cyclobutane-1-carboxylic acid ethyl ester Hydrolysis of syn-hydantoin (FIG. 1, Step 1)
250 mL of a saturated barium hydroxide solution was added to 6.15 g (corresponding to 25 mmol) of syn-5-(3-benzyloxycyclobutane)hydantoin and refluxed under heating in an oil bath at 114° C. for 24 hours or longer. Then, TLC analysis was performed using, as mobile solvents, two kinds of systems: chloroform/methanol=5/1 (Rf value of syn-hydantoin=around 0.6) and chloroform/methanol=95/1 (Rf value of syn-hydantoin=around 0.3), and the completion of the reaction was confirmed (by coloration with UV and phosphomolybdic acid).

After the completion of the reaction was confirmed, the reaction solution was cooled to room temperature, and about 24 mL of 1 mol/mL sulfuric acid was added to neutralize the reaction solution. After the neutralization, the reaction solution was further stirred at room temperature for 5 minutes, and the formed precipitate was removed by filtration. The filtrate was concentrated to yield 5.67 g of syn-1-amino-3-benzyloxycyclobutane-1-carboxylic acid as white crystals.

Ethyl Esterification (FIG. 1, Step 2)
5.67 g of syn-1-amino-3-benzyloxycyclobutane-1-carboxylic acid, which had been fully dried to remove water, was dissolved in 200 mL of ethanol. To this solution, 9.5 mL (corresponding to 75 mmol) of triethylamine was added and cooled at −78° C. for 20 minutes, and then 4.6 mL (corresponding to 62.5 mmol) of thionyl chloride was added. The reaction solution was stirred at 0° C. for 1 hour and at room temperature for 1 hour, followed by heating under reflux in an oil bath at 95° C. overnight. The completion of the reaction was confirmed by TLC analysis using a mobile solvent of chloroform/methanol=95/1 (Rf value of the target compound=around 0.6) (confirmed by coloration with UV and phosphomolybdic acid). After the completion of the reaction was confirmed, the reaction solution was concentrated under reduced pressure to yield 7.64 g of syn-1-amino-3-benzyloxycyclobutane-1-carboxylic acid ethyl ester as white crystals.

Addition of Boc (FIG. 1, Step 3)
7.64 g of syn-1-amino-3-benzyloxycyclobutane-1-carboxylic acid ethyl ester was dissolved in 250 mL of a mixed solution of ethanol/triethylamine=9/1. After the solution was cooled in an ice bath for 15 minutes, 8.6 mL (corresponding to 37.5 mmol) of di-t-butyl dicarbonate was added to the solution and stirred at room temperature overnight. The completion of the reaction was confirmed by TLC analysis using a mobile solvent of hexane/ethyl acetate=1:1 (Rf value of the target compound=around 0.6) (confirmed by coloration with UV and molybdic acid). After the completion of the reaction was confirmed, the reaction solution was concentrated under reduced pressure to yield white crystals as a residue. To the residue, 150 mL of cooled ethyl acetate and 150 mL of 0.5 mol/L cooled hydrochloric acid were added, stirred at room temperature for 5 minutes, and left to stand until separation occurred. The organic layer was extracted and washed with 150 mL of water twice, with 150 mL of a saturated aqueous sodium hydrogencarbonate solution, with 150 mL of water twice and with 150 mL of a saturated saline solution twice in this order, dried with anhydrous sodium sulfate, and concentrated under reduced pressure to yield yellow oily matter. Separately, the water layer was extracted and washed with 150 mL of ethyl acetate twice, with 150 mL of water twice and with 150 mL of a saturated saline solution in this order, dried with anhydrous sodium sulfate, and concentrated under reduced pressure to recover a small amount of yellow oily matter. By these operations, 8.82 g of light yellow oily matter was obtained. The residue was purified by silica gel column chromatography (hexane/ethyl acetate=1/1) to yield 8.04 g (corresponding to 23 mmol) of syn-1-(N-(t-butoxycarbonyl)amino)-3-benzyloxy-cyclobutane-1-carboxylic acid ethyl ester as white crystals.

Debenzylation (FIG. 2, Step 4)
To 8.04 g (corresponding to 23 mmol) of syn-1-(N-(t-butoxycarbonyl)amino)-3-benzyloxy-cyclobutane-1-carboxylic acid ethyl ester, were added 150 mL of ethanol and then 960 mg of palladium-on-activated carbon (10% palladium) to perform replacement with hydrogen under stirring at room temperature overnight. After the reaction, palladium-on-activated carbon was removed by filtration using Celite, and the filtrate was concentrated under reduced pressure to yield 5.74 g of white crystals as a residue. The reaction was traced by TLC analysis using a mobile solvent of hexane/ethyl acetate=1/1 (Rf value of the target compound of reaction=around 0.2) (confirmed by coloration with UV and ninhydrin) to confirm the completion of the reaction. Then, the residue was purified by silica gel column chromatography (hexane/ethyl acetate=1/1, hexane/ethyl acetate=4/1) to yield 5.36 g (corresponding to 20.7 mmol) of syn-1-(N-(t-butoxycarbonyl)amino)-3-hydroxy-cyclobutane-1-carboxylic acid ethyl ester as white crystals.

Triflation (FIG. 3, Step 5)

2.07 g (8 mmol) of syn-1-(N-(t-butoxycarbonyl)amino)-3-hydroxy-cyclobutane-1-carboxylic acid ethyl ester was dissolved in 26 mL of pyridine and stirred in an ice bath for 20 minutes. Then, 2.0 mL (corresponding to 12 mmol) of trifluoromethanesulfonic anhydride was added and stirred for 30 minutes. The reaction was traced by TLC analysis using a mobile solvent of hexane/diethyl ether=1:1 (Rf value of the target compound of reaction=around 0.6) (confirmed by coloration with ninhydrin) to confirm the completion of the reaction. After confirming the completion of the reaction, 100 mL of water and 100 mL of ether were added to the reaction solution, and extraction and washing were performed with 100 mL of 1 mol/L hydrochloric acid twice, with 100 mL of water twice and with 100 mL of a saturated saline solution twice in this order. After drying with anhydrous sodium sulfate, concentration under reduced pressure was performed to yield 2.78 g of light yellow crystals. The reaction mixture was purified by silica gel chromatography (hexane/diethyl ether=3/1) to yield white crystals, and the resultant white crystals were again recrystallized using pentane/diethyl ether to yield 1.84 g (corresponding to 4.7 mmol) of syn-1-(N-(t-butoxycarbonyl)amino)-3-[((trifluoromethyl)sulfonyl)oxy]-cyclobutane-1-carboxylic acid ethyl ester.

Comparative Examples 1-5, Examples 1-8

[$^{18}$F]fluoride ion-containing $H_2{}^{18}O$ was allowed to pass through an anion-exchange column to adsorb and collect [$^{18}$F]fluoride ion on the column. Then, 0.3 mL of a solution of potassium carbonate at a concentration shown in Table 1 was passed through to elute the [$^{18}$F]fluoride ion, 0.3 mL of water was further passed through, and combined with the eluate. To this solution, 1.5 mL of acetonitrile solution of Kryptofix 222 (under trade name, manufactured by Merck & Co., Inc.) in an amount shown in Table 1 was added, and radioactivity of the resulting mixture was measured (A: measured radioactivity in Table 2).

Then, the mixture was heated to 110° C. to evaporate water and acetonitrile, and was subjected to azeotropic distillation with addition of acetonitrile (0.5 mL×2), followed by evaporation to dryness. To the mixture, a solution of syn-1-(N-(t-butoxycarbonyl)amino)-3-[((trifluoromethyl)sulfonyl)oxy]-cyclobutane-1-carboxylic acid ethyl ester (hereinafter referred to as Boc-TfACBC) in an amount shown in Table 1 in acetonitrile in an amount shown in Table 1 was added, and heated at 83° C. for 3 minutes under stirring. Then, the solution was allowed to cool for 5 minutes at room temperature, 4 mL of diethyl ether was added to the solution, and the mixture was allowed to pass through Sep-Pak Silica (under trade name, manufactured by Japan Waters) to yield an acetonitrile/diethyl ether solution of [$^{18}$F]Boc-FACBC as a [$^{18}$F]fluorine-labeled compound. Radioactivity was measured, and the resulting radioactivity B (refers to Table 2) was used for the calculation of [$^{18}$F]fluorination yield. Also, TLC analysis was conducted for the resulting [$^{18}$F]Boc-FACBC to determine a radiochemical purity using the above equation (1).

Meanwhile, the experiment on each condition was conducted once in Comparative Examples 1 and 3 and Example 3, twice in Comparative Examples 2 and 4 and Example 8, four times in Example 4, and three times in others.

TABLE 1

Experiment conditions in each Example and Comparative Example (Amount of each raw material to be used)

| | Concentration of potassium carbonate (mmol/L) | Amount of Kryptofix 222 to be used (μmol) | Amount of Boc-TfACBC (μmol) | Ratio of Kryptofix 222/Boc-TfACBC | Added amount of acetnitrile (mL) |
|---|---|---|---|---|---|
| Comparative Example 1 | 22 | 13 | 40 | 0.33 | 1 |
| Comparative Example 2 | 40 | 24 | 80 | 0.33 | 1 |
| Comparative Example 3 | 66.7 | 53 | 80 | 0.66 | 1 |
| Comparative Example 4 | 100 | 60 | 80 | 0.75 | 1 |
| Comparative Example 5 | 66.7 | 53 | 40 | 1.3 | 1 |
| Example 1 | 100 | 79.5 | 60 | 1.3 | 1 |
| Example 2 | 133 | 80 | 80 | 1.0 | 1 |
| Example 3 | 133 | 93 | 80 | 1.2 | 1 |
| Example 4 | 133 | 106 | 80 | 1.3 | 1 |
| Example 5 | 133 | 106 | 80 | 1.3 | 1.5 |
| Example 6 | 133 | 120 | 80 | 1.5 | 1 |
| Example 7 | 167 | 133 | 100 | 1.3 | 1 |
| Example 8 | 133 | 160 | 80 | 2.0 | 1 |

TABLE 2

Measured values of radioactivity in each Example and Comparative Example (values corrected back to initiation of synthesis)

| | A (MBq) | B (MBq) |
|---|---|---|
| Comparative Example 1 | 59.80 | 24.38 |
| Comparative Example 2 | 1: 159.84, 2: 149.13 | 1: 88.73, 2: 69.59 |
| Comparative Example 3 | 320.11 | 203.06 |
| Comparative Example 4 | 1: 421.71, 2: 347.29 | 1: 308.17, 2: 216.28 |
| Comparative Example 5 | 1: 211.91, 2: 187.64, 3: 371.63 | 1: 122.40, 2: 119.11, 3: 245.90 |
| Example 1 | 1: 278.90, 2: 175.47, 3: 356.11 | 1: 193.63, 2: 117.86, 3: 252.20 |
| Example 2 | 1: 500.23, 2: 273.51, 3: 355.39 | 1: 293.15, 2: 184.08, 3: 239.33 |
| Example 3 | 461.47 | 326.44 |
| Example 4 | 1: 112.29, 2: 445.79, 3: 149.01, 4: 126.74 | 1: 86.33, 2: 332.52, 3: 113.81, 4: 97.44 |
| Example 5 | 1: 242.47, 2: 153.66, 3: 135.65 | 1: 165.59, 2: 101.35, 3: 93.59 |
| Example 6 | 1: 123.95, 2: 433.30, 3: 330.94 | 1: 86.20, 2: 297.44, 3: 245.92 |
| Example 7 | 1: 128.58, 2: 123.51, 3: 301.16 | 1: 98.64, 2: 86.89, 3: 218.30 |
| Example 8 | 1: 123.10, 2: 112.36 | 1: 93.45, 2: 84.60 |

Results are shown in Table 3 and FIGS. 4-6.

A ratio of Kryptofix 222 used as a phase transfer catalyst to a precursor Boc-TfACBC (hereinafter referred to as a ratio of phase transfer catalyst/precursor) was calculated, and a relation with a yield of [$^{18}$F]fluorination was investigated. The results are shown in FIG. 4. As it is clear from this figure, under the condition in which the ratio of phase transfer catalyst/precursor is less than 0.7, the yield of [$^{18}$F]fluorination of [$^{18}$F]Boc-FACBC was remarkably improved with increase of the ratio of phase transfer catalyst/precursor. Under the condition in which the ratio of phase transfer catalyst/precursor is not less than 0.7, the data indicated a substantially constant yield although there was a data showing a low yield of [$^{18}$F]fluorination (in Comparative Example 5), and the yield of [$^{18}$F]fluorination under this condition was about 30-50% higher than the conventional process (Comparative Example 1).

A relation between the concentration of potassium ions in acetonitrile of the reaction solution and the yield of [$^{18}$F]fluorination is shown in FIG. 5. As it is clear from FIG. 5, under the condition in which the concentration of potassium ions is less than 27 mmol/L, the yield of [$^{18}$F]fluorination was remarkably improved with increase of the concentration of potassium ions, and at a concentration higher than this, the yield was almost constant. A relation between the concentration of Kryptofix in acetonitrile of the reaction solution and the yield of [$^{18}$F]fluorination is shown in FIG. 6. As it is clear from FIG. 6, under the condition in which the concentration of Kryptofix in acetonitrile of the reaction solution (indicated as concentration of phase transfer catalyst in FIG. 6) is less than 70 mmol/L, the [$^{18}$F]fluorination of [$^{18}$F] Boc-FACBC was remarkably increased with increase of the concentration of Kryptofix, and at a concentration higher than this, the yield was almost constant. Therefore, it has been revealed that [$^{18}$F]Boc-FACBC can be prepared with a high yield of [$^{18}$F]fluorination under the conditions in which the concentration of potassium ions is not less than 27 mmol/L, and the concentration of phase transfer catalyst is not less than 70 mmol/L. Also, it has been indicated that by setting these conditions in addition to the above described condition where the ratio of phase transfer catalyst/precursor is not less than 0.7, the condition (Comparative Example 5) showing a low yield under the conditions where the ratio of phase transfer catalyst/precursor is not less than 0.7 can be removed, and thus a high yield of [$^{18}$F]fluorination can be more stably achieved.

From the above results, it has been indicated that [$^{18}$F]Boc-FACBC can stably be obtained in high yield by combining the condition in which the ratio of phase transfer catalyst/precursor is not less than 0.7, the condition in which the concentration of potassium ions is not less than 27 mmol/L, and the condition in which the concentration of phase transfer catalyst is not less than 70 mmol/L, in the [$^{18}$F]fluorination.

TABLE 3

Yield of [$^{18}$F] fluorination and radiochemical purity of the compounds obtained in each Example and Comparative Example

|  | Yield of [$^{18}$F] fluorination % | Radiochemical purity % |
|---|---|---|
| Comparative Example 1 | 24.16 | 59.27 |
| Comparative Example 2 | 38.13 | 74.77 |
| Comparative Example 3 | 54.75 | 86.32 |
| Comparative Example 4 | 59.80 | 88.24 |
| Comparative Example 5 | 56.66 | 90.65 |
| Example 1 | 65.95 | 95.33 |
| Example 2 | 61.39 | 95.36 |
| Example 3 | 64.87 | 91.70 |
| Example 4 | 73.53 | 96.52 |
| Example 5 | 65.33 | 96.43 |
| Example 6 | 67.98 | 95.92 |
| Example 7 | 68.38 | 93.37 |
| Example 8 | 70.73 | 93.57 |

Examples 9-43

At the reaction temperature of 40-100° C., the following experiments were performed in order to confirm that [$^{18}$F] Boc-FACBC can be produced in good yield according to the producing process of the present invention.

[$^{18}$F]fluoride ion-containing H$_2$$^{18}$O was allowed to pass through an anion-exchange column to adsorb and collect [$^{18}$F]fluoride ion on the column. Then, 0.3 mL of a solution of potassium carbonate at a concentration of 133 mmol/L was passed through the column to elute [$^{18}$F]fluoride ion, 0.3 mL of water was further passed through, and combined with the eluate. To this solution, a solution of 106 µmol of Kryptfix 222 (trade name, manufactured by Merck & Co., Inc.) in 1.5 mL of acetonitrile was added.

Then, the mixture was heated to 110° C. to evaporate water, and was subjected to azeotropic distillation with addition of acetonitrile (0.5 mL×2), followed by evaporation to dryness. To this mixture, a solution of 80 µmol of Boc-TfACBC in 1 mL of acetonitrile was added, and the reaction solution was stirred for a time period shown in Tables 4a-4d at a temperature shown in Tables 4a-4e, and was allowed the radioactive fluorination to proceed. The resulting reaction solution was subjected to TLC analysis, and an area % of [$^{18}$F]Boc-FACBC was determined and used as an index for yield of [$^{18}$F]fluorination.

Meanwhile, the radioactivity used in each experiment was 414-759 MBq.

TLC analysis conditions:
TLC plate: Silica Gel 60 F$_{254}$ (trade name; manufactured by Merck & Co., Inc.)
Mobile phase: Diethylether/hexane=1/1
Detector: Rita Star (trade name; manufactured by raytest)

TABLE 4a

Reaction temperature and reaction time in each Example

| | Example 9 | Example 10 | Example 11 | Example 12 | Example 13 | Example 14 | Example 15 |
|---|---|---|---|---|---|---|---|
| Reaction temperature C.° | 40 | 50 | 60 | 70 | 80 | 90 | 100 |
| Reaction time min | 3 | 3 | 3 | 3 | 3 | 3 | 3 |

TABLE 4b

Reaction temperature and reaction time in each Example

| | Example 16 | Example 17 | Example 18 | Example 19 | Example 20 | Example 21 | Example 22 |
|---|---|---|---|---|---|---|---|
| Reaction temperature C.° | 40 | 50 | 60 | 70 | 80 | 90 | 100 |
| Reaction time min | 5 | 5 | 5 | 5 | 5 | 5 | 5 |

TABLE 4c

Reaction temperature and reaction time in each Example

| | Example 23 | Example 24 | Example 25 | Example 26 | Example 27 | Example 28 | Example 29 |
|---|---|---|---|---|---|---|---|
| Reaction temperature C.° | 40 | 50 | 60 | 70 | 80 | 90 | 100 |
| Reaction time min | 7 | 7 | 7 | 7 | 7 | 7 | 7 |

TABLE 4d

Reaction temperature and reaction time in each Example

| | Example 30 | Example 31 | Example 32 | Example 33 | Example 34 | Example 35 | Example 36 |
|---|---|---|---|---|---|---|---|
| Reaction temperature C.° | 40 | 50 | 60 | 70 | 80 | 90 | 100 |
| Reaction time min | 10 | 10 | 10 | 10 | 10 | 10 | 10 |

TABLE 4e

Reaction temperature and reaction time in each Example

| | Example 37 | Example 38 | Example 39 | Example 40 | Example 41 | Example 42 | Example 43 |
|---|---|---|---|---|---|---|---|
| Reaction temperature C.° | 40 | 50 | 60 | 70 | 80 | 90 | 100 |
| Reaction time min | 15 | 15 | 15 | 15 | 15 | 15 | 15 |

The results are shown in Tables 5a-5e. As it is clear from these results, under the conditions in which the reaction time is 3-15 minutes, the yield of [$^{18}$F]fluorination showed a good value of not less than 62% at all the reaction temperatures. Also, no significant change was seen in the yield of [$^{18}$F] fluorination at the reaction temperature of not less than 90° C., and thus it has been suggested that a good yield of [$^{18}$F] fluorination can be obtained at a reaction temperature of 40-90° C.

Also, under the conditions in which the reaction temperature was 50-80° C., the yield of [$^{18}$F]fluorination reached not less than 70% in all the reaction time, and under the conditions in which the reaction temperature was 60-70° C., the yield of [$^{18}$F]fluorination reached not less than 80% in all the reaction time.

On the other hand, referring to the reaction time, a particularly good yield of [$^{18}$F]fluorination was obtained when the reaction time was 3-7 min.

Therefore, it has been indicated that in the reaction time of 3-15 min, a good yield of [$^{18}$F]fluorination can be achieved under a condition in which the reaction temperature is 40-90° C. or more, a better yield of [$^{18}$F]fluorination can be obtained under a condition of 50-80° C., and a particularly good yield of [$^{18}$F]fluorination can be achieved under a condition of 60-70° C.

In addition, it has been indicated that the reaction time of not less than 3 minutes is sufficient, and the reaction time of 3-7 min is more preferable.

TABLE 5a

Yield of [$^{18}$F] fluorination in each Example

| | Example 9 | Example 10 | Example 11 | Example 12 | Example 13 | Example 14 | Example 15 |
|---|---|---|---|---|---|---|---|
| Reaction temperature C.° | 40 | 50 | 60 | 70 | 80 | 90 | 100 |
| Reaction time min | 3 | 3 | 3 | 3 | 3 | 3 | 3 |
| Yield of [$^{18}$F] fluorination % | 62 | 74 | 82 | 86 | 79 | 74 | 74 |

TABLE 5b

Yield of [$^{18}$F] fluorination in each Example

| | Example 16 | Example 17 | Example 18 | Example 19 | Example 20 | Example 21 | Example 22 |
|---|---|---|---|---|---|---|---|
| Reaction temperature C.° | 40 | 50 | 60 | 70 | 80 | 90 | 100 |
| Reaction time min | 5 | 5 | 5 | 5 | 5 | 5 | 5 |
| Yield of [$^{18}$F] fluorination % | 70 | 80 | 83 | 84 | 78 | 70 | 69 |

TABLE 5c

Yield of [$^{18}$F] fluorination in each Example

| | Example 23 | Example 24 | Example 25 | Example 26 | Example 27 | Example 28 | Example 29 |
|---|---|---|---|---|---|---|---|
| Reaction temperature C.° | 40 | 50 | 60 | 70 | 80 | 90 | 100 |
| Reaction time min | 7 | 7 | 7 | 7 | 7 | 7 | 7 |
| Yield of [$^{18}$F] fluorination % | 74 | 81 | 81 | 83 | 76 | 72 | 73 |

TABLE 5d

Yield of [$^{18}$F] fluorination in each Example

| | Example 30 | Example 31 | Example 32 | Example 33 | Example 34 | Example 35 | Example 36 |
|---|---|---|---|---|---|---|---|
| Reaction temperature C.° | 40 | 50 | 60 | 70 | 80 | 90 | 100 |

TABLE 5d-continued

Yield of [$^{18}$F] fluorination in each Example

| | Example 30 | Example 31 | Example 32 | Example 33 | Example 34 | Example 35 | Example 36 |
|---|---|---|---|---|---|---|---|
| Reaction time min | 10 | 10 | 10 | 10 | 10 | 10 | 10 |
| Yield of [$^{18}$F] fluorination % | 76 | 83 | 83 | 81 | 76 | 67 | 70 |

TABLE 5e

Yield of [$^{18}$F] fluorination in each Example

| | Example 37 | Example 38 | Example 39 | Example 40 | Example 41 | Example 42 | Example 43 |
|---|---|---|---|---|---|---|---|
| Reaction temperature C.° | 40 | 50 | 60 | 70 | 80 | 90 | 100 |
| Reaction time min | 15 | 15 | 15 | 15 | 15 | 15 | 15 |
| Yield of [$^{18}$F] fluorination % | 78 | 83 | 81 | 82 | 74 | 69 | 68 |

INDUSTRIAL APPLICABILITY

The process for producing a radioactive fluorine-labeled organic compound according to the present invention can be suitably used for production of a radioactive fluorine-labeled organic compound including [$^{18}$F]Boc-FACBC which is used for production of novel diagnostic agents.

Figure 1:
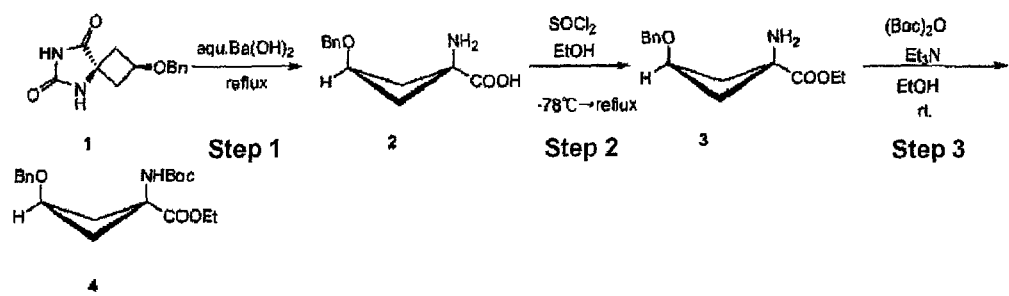
FIG. 1 shows a scheme of synthesis of syn-1-(N-(t-butoxy-carbonyl)amino)-3-benzyloxy-cyclobutane-1-carboxylic acid ethyl ester.
Figure 2:
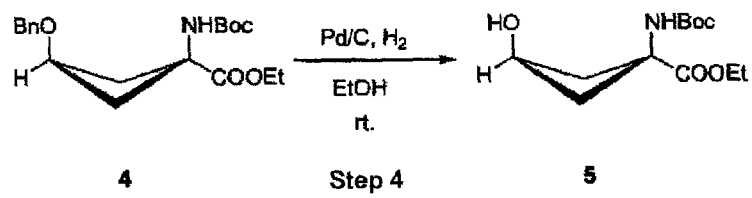
FIG. 2 shows a scheme of synthesis of syn-1-(N-(t-butoxy-carbonyl)amino)-3-hydroxy-cyclobutane-1-carboxylic acid ethyl ester.
Figure 3:
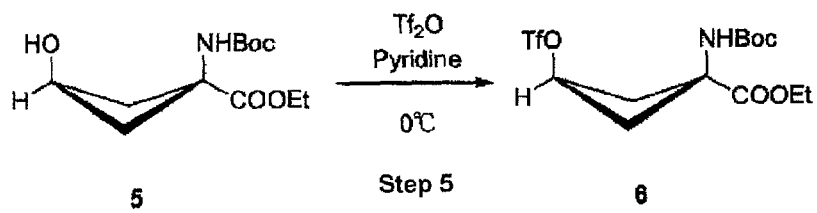
FIG. 3 shows a scheme of synthesis of syn-1-(N-(t-butoxy-carbonyl)amino)-3-[((trifluoromethyl)sulfonyl)oxy]-cyclobutane-1-carboxylic acid ester.
Figure 4:
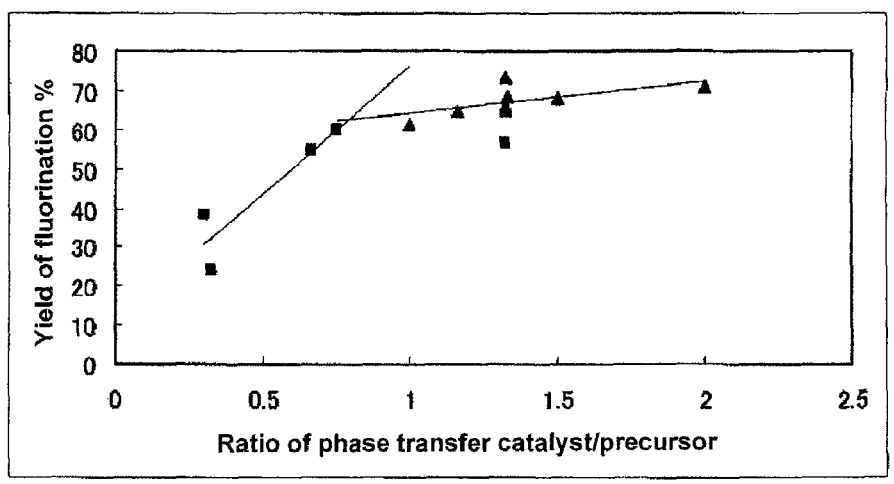
FIG. 4 is a graph which shows a relation between a ratio of phase transfer catalyst/labeling precursor and a yield of fluorination (triangle: Examples, square: Comparative Examples).
Figure 5:
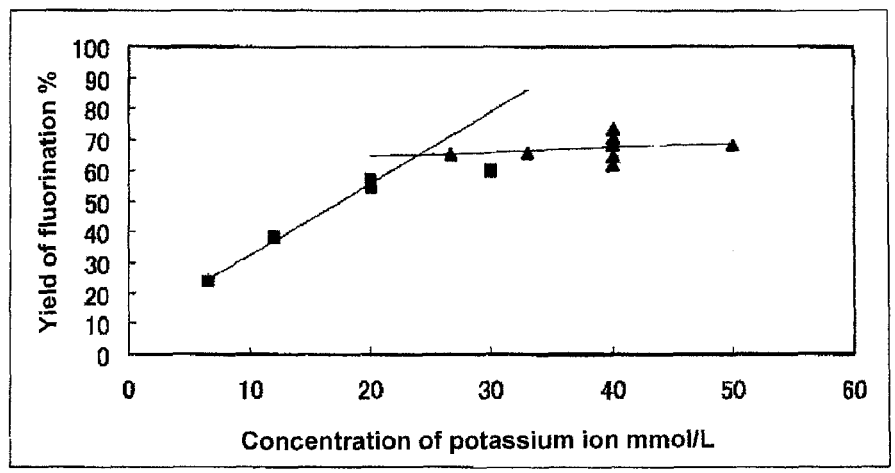
FIG. 5 is a graph which shows a relation between a concentration of potassium ions and a yield of fluorination (triangle: Examples, square: Comparative Examples).
Figure 6:
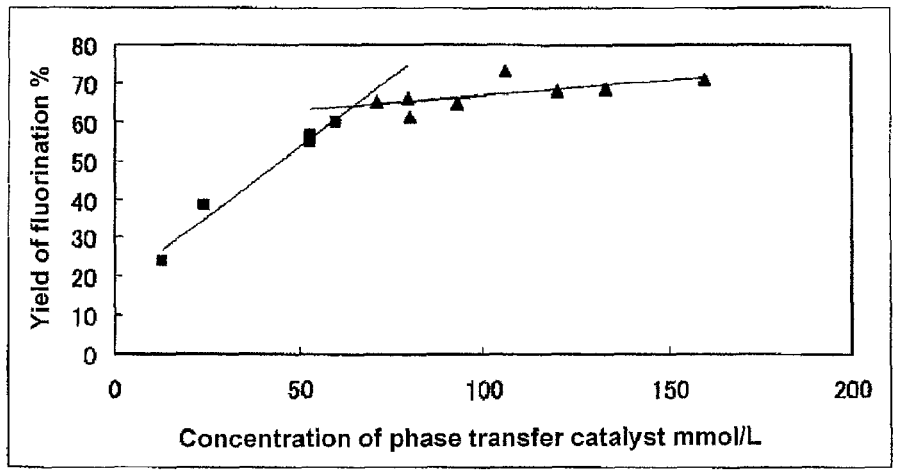
FIG. 6 is a graph which shows a relation between a concentration of phase transfer catalyst and a yield of fluorination (triangle: Examples, square: Comparative Examples).

The invention claimed is:

1. A process for producing a radioactive fluorine-labeled organic compound, which comprises subjecting a compound represented by the following formula (1):

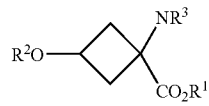

(1)

wherein $R^1$ is a straight or branched alkyl chain with 1-10 carbon atoms or an aromatic substituent, $R^2$ is a straight or branched haloalkylsulfonic acid substituent with 1-10 carbon atoms, a straight or branched alkylsulfonic acid substituent with 1-10 carbon atoms, a fluorosulfonic acid substituent or an aromatic sulfonic acid substituent, and $R^3$ is a protective group to a heating step in an inert organic solvent in a presence of a phase transfer catalyst, $^{18}$F ions and potassium ions, so as to obtain a compound represented by the following formula (2):

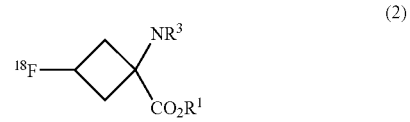

(2)

wherein $R^1$ is a straight or branched alkyl chain with 1-10 carbon atoms or an aromatic substituent, $R^3$ is a protective group, in which the heating step is conducted at a heating temperature of 40-90° C., and the phase transfer catalyst is contained in the inert organic solvent at a concentration of not less than 70 mmol/L, potassium ions are contained in the inert organic solvent at a concentration of not less than 27 mmol/L, and the phase transfer catalyst is used in a molar ratio of not less than 0.7 relative to the compound represented by the formula (1).

2. The process according to claim 1, wherein the compound represented by the formula (1) is contained in the inert organic solvent at a concentration of not less than 50 mmol/L.

3. The process according to claim 1 or 2, which comprises:
a step of obtaining a mixture of a phase transfer catalyst, $^{18}$F ions and potassium ions; and
a radioactive fluorinating step of adding a compound represented by said formula (1) and an inert organic solvent to the above mixture, and maintaining the resulting reaction solution at a temperature of 40-90° C. under stirring so as to obtain a compound represented by said formula (2).

4. The process according to claim 1, wherein the heating step is conducted at a heating temperature of 50-80° C.

5. The process according to claim 1, wherein the heating step is conducted at a heating temperature of 60-70° C.

6. The process according to claim 1, wherein the concentration and amount of said phase transfer catalyst is adjusted so that the molar amount of said phase transfer catalyst relative to potassium ion is about 1.3.

7. The process according to claim 1, wherein the compound represented by the formula (1) is contained in the inert organic solvent at a concentration of not less than 60 mmol/L.

8. The process according to claim 1, wherein the compound represented by the formula (1) is contained in the inert organic solvent at a concentration of not less than 70 mmol/L.

9. The process according to claim 1, wherein the phase transfer catalyst is used in an equimolar or greater ratio relative to the compound represented by the formula (1).

10. A process according to claim 1, wherein the phase transfer catalyst is used in a molar ratio between not less than 0.7 and not more than 2 relative to the compound represented by the formula (1).

11. A process according to claim 10, wherein the phase transfer catalyst is used in a molar ratio between more than 0.75 and not more than 2 relative to the compound represented by the formula (1).

12. A process according to claim 11, wherein the phase transfer catalyst is used in a molar ratio between the equimolar ratio and not more than 2 relative to the compound represented by the formula (1).

13. A process according to claim 1, wherein the phase transfer catalyst is contained in the inert organic solvent at a concentration between not less than 70 mmol/L and not more than 160 mmol/L.

* * * * *